United States Patent [19]

Rettegi et al.

[11] Patent Number: 4,632,928
[45] Date of Patent: Dec. 30, 1986

[54] PYRAZOLE DERIVATIVES WITH AN ERGOLINE SKELETON, THEIR ACID ADDITION SALTS, AND A PROCESS FOR THE PREPARATION THEREOF

[75] Inventors: Tivadar Rettegi; Erzsébet Magó née Karácsony; Lajos Toldy; József Borsy; Ilona Berzétei; András Rónai; Aliz Druga; György Cseh, all of Budapest, Hungary

[73] Assignee: Richter Gedeon Vegyeszeti Gyar R.T., Budapest, Hungary

[21] Appl. No.: 615,387

[22] Filed: May 30, 1984

[30] Foreign Application Priority Data

Mar. 6, 1983 [HU] Hungary .............................. 2001/83

[51] Int. Cl.[4] .................... C07D 457/02; A61K 31/48
[52] U.S. Cl. ........................................ 514/288; 546/67
[58] Field of Search ......................... 546/67; 424/261; 514/288

[56] References Cited

U.S. PATENT DOCUMENTS 3,557,118  1/1971  Arcamone et al. ................ 424/261
4,134,987  1/1979  Huppatz ............................. 548/377

FOREIGN PATENT DOCUMENTS 2056437  3/1981  United Kingdom ................ 546/67

OTHER PUBLICATIONS

Berde and Schild, *Ergot Alkaloids and Related Compounds*, Springer-Verlag, New York, (1978), p. 184.

Primary Examiner—G. Hendricks
Attorney, Agent, or Firm—Keil & Weinkauf

[57] ABSTRACT

The invention relates to novel pyrazole derivatives with an ergoline skeleton of the general formula I,

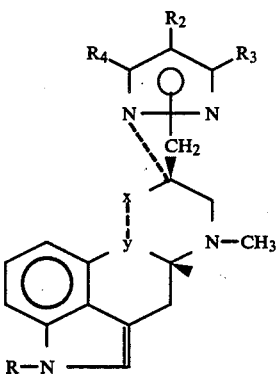

wherein
x ... y stands for a

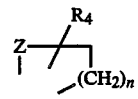 group, R is a hydrogen atom or methyl group,
$R_1$ stands for a hydrogen atom, $C_{1-4}$ alkyl, carbethoxy or pyridyl-group,
$R_2$ stands for a hydrogen atom, $C_{1-4}$ alkyl, allyl, $C_{2-4}$ oxoalkyl-, $C_{2-4}$ hydroxyalkyl or $C_{2-4}$ hydroxyiminoalkyl group,
$R_3$ stands for a hydrogen atom, $C_{1-4}$ alkyl, hydroxy or pyridyl group, furthermore
$R_2$ and $R_3$ may stand together for a group of general formula (II), $$Z \underset{\diagdown (CH_2)_n}{\overset{R_4}{\diagup}} \qquad \text{II}$$

wherein
Z stands for a methylene, carbonyl, hydroxymethylene or hydroxyiminomethylene group,
$R_4$ stands for a hydrogen atom or one or two $C_{1-4}$ alkyl group(s), and
n is 1 or 2, and pharmaceutically acceptable salts thereof.

Furthermore the invention relates to a process for the preparation of these compounds.

The novel compounds are potent $PGF_{2\alpha}$ receptor antagonists.

5 Claims, No Drawings

PYRAZOLE DERIVATIVES WITH AN ERGOLINE SKELETON, THEIR ACID ADDITION SALTS, AND A PROCESS FOR THE PREPARATION THEREOF

The invention relates to novel pyrazole derivatives with an ergoline skeleton of the general formula (I),

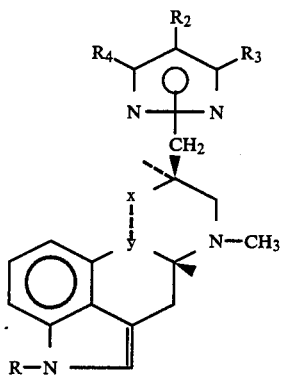

wherein
x ... y stands for a

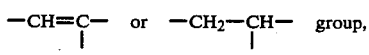

R means a hydrogen atom or methyl group,
$R_1$ stands for a hydrogen atom, $C_{1-4}$ alkyl, carbethoxy or pyridyl group,
$R_2$ means a hydrogen atom, $C_{1-4}$ alkyl, allyl, $C_{2-4}$ oxoalkyl, $C_{2-4}$ hydroxyalkyl or $C_{2-4}$ hydroxyiminoalkyl group,
$R_3$ stands for a hydrogen atom, $C_{1-4}$ alkyl, hydroxy or pyridyl group, furthermore
$R_2$ and $R_3$ may stand together for a group of general formula (II),

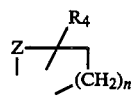

wherein
Z stands for a methylene, carbonyl, hydroxymethylene or hydroxyiminomethylene group,
$R_4$ stands for a hydrogen atom or one or two $C_{1-4}$ alkyl group(s), and
n is 1 or 2,
and pharmaceutically acceptable salts thereof, as well as to a process for their preparation, and to pharmaceutical compositions containing these compounds as active agent.

The effect of compounds with an ergoline skeleton on the uterine musculature is known for a long time. The most potent uterotonic compounds, inducing uterine contraction, widely applied in therapy, belong to this group of substances (methylergometrin, ergometrin, ergotamine). Within the same family of compounds there are, however, also uterine relaxants (bromocryptine, dihydroergotamine, hydergine). Thus the ergoline skeleton undoubtedly has a specific affinity to the uterine musculature.

Exploiting this phenomenon it was our aim to prepare novel compounds with an ergoline skeleton which are competitive inhibitors of the receptor activity of the most potent endogeneous compound inducing uterine contraction, prostaglandin $F_{2alpha}$ ($PGF_{2alpha}$=9α,1-1α,15(S)-trihydroxy-5cis, 13trans-prostadienoic acid). Such compounds are unknown yet, though they could be of major therapeutic importance in obstetrics, gynecology and neonatology (dysmenorrhea, anovulation, gestational toxicosis, habitual abortus, premature delivery, occlusion of Botallo's duct, etc.), in conditions where there is a pathogenic overproduction of the highly active, endogenic uterotonic agent. Due to the pathophysiological effect of $PGF_{2alpha}$ these compounds also could exhibit advantageous therapeutic activity in other conditions, (bronchial asthma, disturbances in gastrointestinal motility, rheumatic conditions, anaphylaxis, etc).

Pyrazole derivatives with an ergoline skeleton were first mentioned by A. Hofmann in Swiss Pat. No. 392,531, but the (pyrazolylcarbonyl)-ergoline compound described by him was acid sensitive, and only the intermediary in the conversion of lysergic acid hydrazide to lysergic acid could be isolated. The inventors of U.S. Pat. No. 3,184,234 describe pyrazole-carboxamido-ergoline derivatives exhibiting antiulcer activity.

The pyrazol-1-yl-methylen-ergoline derivatives of the invention are different from the former compounds both as regards biological and chemical properties, and up till now were not reported in the literature.

The new compounds of the general formula (I) can be prepared according to the invention by reacting a hydrazine compound of the general formula (III)

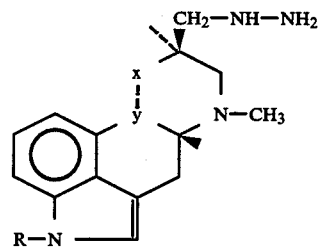

wherein x ... y and R have the same meaning as above,
(a) with a beta-diketone of the general formula (IV),

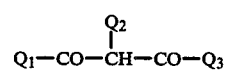

wherein $Q_1$ and $Q_2$ stand, independently from each other, for a $C_{1-4}$ alkyl, ethoxy, carbethoxy or pyridyl group and $Q_3$ stands for a hydrogen atom, $C_{1-4}$ alkyl, allyl or $C_{2-4}$ oxoalkyl group,
or
(b) with a cycloalkanone of the general formula (V)

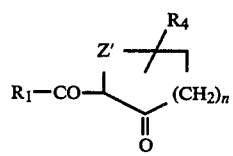

wherein $R_1$ stands for a hydrogen atom, a $C_{1-4}$ alkyl or pyridyl group, Z' stands for a methylene or carbonyl group, $R_4$ represents a hydrogen atom, or one or two $C_{1-4}$ alkyl group(s), and n is 1 or 2,
then, if desired, the compound of general formula (I), obtained either by process (a) or (b), is reduced or converted into an oxime and/or converted to a pharmaceutically acceptable salt.

At the use of asymmetric beta-diketones a mixture of isomers may be formed which can be separated into their components by column chromatography. In compounds where the position of the ergoline-methylene group on the pyrazole ring is not elucidated yet, the alternative structure is indicated, as usual, by a figure in brackets.

According to a preferred process (a) or (b) a diketone, either of general formula IV or V, is added at room temperature to a compound of general formula (III), dissolved in a lower alcohol, preferably in ethanol, tetrahydrofuran and/or acetonitrile, then the mixture is acidified to pH 3 or 4 by an inorganic or organic acid, preferably hydrochloric acid, and is stirred for 1 hour.

According to another preferred process (a) or (b) compounds of general formula (III) and (IV) or (V) are dissolved in a lower alcohol, preferably methanol, whereupon boron trifluoride is added and the mixture is stirred for 1 hour at room temperature.

According to a further preferred process (a) or (b) compounds of general formula (III) and (IV) or (V) are added to boiling 50 percent aqueous ethanol, after 3 to 5 minutes the reaction mixture is acidified with a strong mineral acid, preferably with hydrochloric acid, then boiling is continued for further 13 to 15 minutes, and the mixture is poured over ice.

At the end of the reaction the product is isolated, purified, if necessary, by column chromatography and, if desired, converted into an acid addition salt.

The starting materials, the hydrazino compounds of general formula (III), can be prepared by the process of Hungarian Patent No. 178,396.

The starting materials of general formula (IV) are known from the literature and can be prepared by known methods [Archiv der Pharmazie 295 (8), 627 to 639 (1962)].

The starting materials of general Formula (V) are also known from the literature and can be prepared by known methods [Acta Chim. Scand. 17, 1801 (1963)].

The compounds of the invention possess valuable biological properties, they are potent $PGF_{2alpha}$ receptor antagonists. In vitro, in the isolated rat uterus (Table 1), and in vivo in rabbits under urethane anesthesis (Table 2) they antagonize the uterine contraction inducing activity of $PGF_{2alpha}$. The competitive antagonist effect of the compounds is selective and protracted, while it fails to influence the uterine contraction inducing effect of other endogeneous compounds, i.e. oxytocin. This would enable their use as spasmolytic agents of new mechanism of action in the field of obstetrics and gynecology for the treatment of dysmenorrhea and anovulation, and the prevention of imminent and habitual abortus and miscarriage.

In addition to the antiprostaglandin effect the compounds of the invention possess further pharmacological properties, namely antiserotonine, hypotensive, prolactine-level reducing, and significant dopamine receptor agonist effect, which may be exploited for the therapy of various conditions, such as bronchial asthma, disturbances in gastrointestinal motility, etc.

The advantageous therapeutical properties of the compounds are accompanied by low toxicity (Table 3).

The planned human dose would amount to 0.5 to 3 mg/kg body weight daily.

According to a still further feature of the present invention there are provided pharmaceutical compositions comprising as active ingredient at least one compound of general formula (I) in association with one or more pharmaceutical carriers or excipients. Such compositions may, for example, be in a form suitable for oral or parenteral administration. Suitable forms include e.g. tablets, capsules and solutions.

TABLE 1

$PGF_{2alpha}$ antagonist effect of the compounds of general formula (I) in vitro in isolated rat uterus

| Method: | 1. J. H. Gaddum and K. A. Hammed: Brit. J. Pharmacol. 9, 240 (1954) |
|---|---|
| | 2. O. Arunlakshana and H. O Schild: Brit. J. Pharmacol. 14, 48–58 (1959) |

| Compound (Example No.) | Percentual inhibition at concentrations of $2 \times 10^{-6}$ M against $1.4 \times 10^{-7}$ M $PGF_{2alpha}$ |
|---|---|
| 1 | 70 |
| 2 | 58 |
| 5 | 46 |
| 9 | 40 |
| 10 | 66 |
| 11 | 80 |
| 14 | 77 |
| 15 | 40 |
| 16 | 18 |
| 17 | 44 |

TABLE 2

In vivo $PGF_{2alpha}$ antagonist effect of pyrazole derivatives of general formula (I) in urethane (1.2 g/kg iv) anesthesized rabbits

| Method: | 1. D. F. Hawkins: Agents Acting on the Uterus. In: Evaluation of Drug Activities: Pharmacometrics. Edited by R. Lawrence and A. L. Bacharach. Academic Press, London, p. 680 (1964) |
|---|---|
| | 2. A. R. Cushny: J. Physiol. 35, 1 (1906) |

| Compound (Example No.) | No. of animals n | Dose mg/kg intraduodenal | Inhibition % | Duration of the effect minute |
|---|---|---|---|---|
| 1 | 12 | 0.3 | 38 | >180 |
|  | 5 | 1.0 | 49 | >180 |
| Hydrogen-fumarate of 1 | 12 | 3.0 | 63 | >180 |
| 9 | 7 | 3.0 | 58 | >180 |
|  | 9 | 10.0 | 68 | >180 |
| 17 | 6 | 10.0 | 55 | 120 |
|  | 6 | 20.0 | 77 | >150 |
| 10 | 3 | 20.0 | 42 | 90 |
| 11 | 3 | 20.0 | 72 | >120 |

$PGF_{2alpha}$ standard dose: 6.25 µg/kg iv

TABLE 3

Acute toxicity of pyrazole derivatives of general formula (I) in CFLP mice

| Method: | Probite analysis according to Litchfield-Wilcoxon [J. Pharm. Exp. Ther. 96, 99 (1949)] | | |
|---|---|---|---|
| Compound (Example No.) | $LD_{50}$ mg/kg | | No. of animals |
| | ip | po | n |
| 1 | 3100 | 2450 | 10 |
| 2 | >100 | >100 | |
| 4 | >100 | >100 | |
| 5 | >100 | >100 | |
| 6 | >200 | 1000 | |
| 7 | >100 | >100 | |
| 8 | >100 | >100 | |
| 9 | >100 | >100 | |
| 10 | >100 | >100 | |
| 11 | >100 | >100 | |
| 14 | >100 | >100 | |
| 15 | >100 | >100 | |

TABLE 3-continued

Acute toxicity of pyrazole derivatives of general formula (I) in CFLP mice

| Method: | Probite analysis according to Litchfield-Wilcoxon [J. Pharm. Exp. Ther. 96, 99 (1949)] | |
|---|---|---|
| 16 | >100 | >100 |
| 17 | >100 | >100 |
| 18 | >100 | >100 |

The following examples are illustrative of the invention without limiting its scope.

EXAMPLE 1

8-beta-[3(5)-Methyl-cyclopentano/4,5(3,4)/pyrazol-1-yl-methylene]-6-methyl-ergol-9-ene 5.37 g (0.02M) of 6-methyl-8-beta-hydrazino-methyl-ergol-9-ene are dissolved at room temperature under vigorous stirring in 100 ml of 50 percent aqueous ethanol, then 3.0 g (0.024M) of 2-acetyl-cyclopentanone are added, and the mixture is acidified with 1N aqueous hydrochloric acid to pH 3 to 4. The mixture is stirred at room temperature in the dark for one hour, then its pH is adjusted to pH 9 with a concentrated ammonium hydroxide solution, thereafter it is diluted with 200 ml of water and is extracted three times with 100 ml of dichloromethane. The combined organic layers are dried over sodium sulfate and are subsequently evaporated to dryness at reduced pressure. The reaction product is purified by column chromatography. The crude product is dissolved in the eluting solvent and layered over a column prepared from 200 g of silicagel. Elution is carried out with a 100:0.17:3.7 mixture of chloroform-water-methanol, and the purity of the compound is controlled by thin-layer chromatography on 0.25 mm silicagel plates (adsorbent Kieselgel G nach Stahl). Length of development 20 cm, visualization with van Urk reagent (E. Stahl: Dünnschichtchnomatographie. Springer Verlag 1967, p. 825). The eluates are evaporated to dryness at reduced pressure and the residue is recrystallized from 150 ml of 96 percent ethanol, yielding colourless needles of 4 g. Further 1 g of the product can be recovered from the mother liquor.

Yield: 70 percent.

Mp.: 214°–215° C., $[\alpha]_D^{20} = +90.3°$ (c=0.2, ethanol).

Hydrogen fumarate salt 1.25 g (0.0035M) of 8-beta-[3(5)-methyl-cyclopentano/4,5(3,4)/pyrazol-1-yl-methylene]-6-methyl-ergol-9-ene are dissolved in 70 ml of warm isopropanol, then 0.402 g (0.0035M) of fumaric acid, dissolved in a mixture of 16 ml of isopropanol and 0.5 ml of water, is added to the hot solution. The hot solution is filtered, evaporated at reduced pressure to half of its volume, then the wall of the flask is scratched till the onset of crystallization, and the mixture is left to stand in the dark overnight at 0° to 5° C., yielding 1.30 g of crystalline 8-beta-[3(5)-methyl-cyclopentano/4,5(3,4)-/pyrazol-1-yl-methylene]-6-methyl-ergol-9-ene hydrogen fumarate. M.p.: 181° to 183° C. (decomposition), $[\alpha]_D^{20} = +81.5°$ (c=0.2, ethanol). Further 0.25 g portion of the product can be obtained by concentrating the mother liquor.

Yield: 94 percent.

EXAMPLE 2

8-beta-[3(5)-Methyl-cyclopentane/4,5(3,4)/pyrazol-1-yl-methylene]-1,6-dimethyl-ergol-9-ene hydrogen maleinate Sodium-amide is prepared from 0.29 g (0.0126 gatom) of metal sodium in 250 ml of anhydrous liquid ammonia, then 1.79 g (0.005M) of 8-beta-[3(5)-methyl-cyclopentano/4,5(3,4)]pyrazol-1-yl-methylene]-6-methyl-ergol-9-ene, dissolved in 20 ml of anhydrous tetrahydrofuran, are added. After 10 minutes the mixture is cooled to −50° C., and dropwise 2.5 g (0.018M) of methyl-iodide in 10 ml of anhydrous ether are added. Then the reaction mixture is left to warm up to the boiling point of liquid ammonia, and it is stirred there for a further 30 minutes. The progress of the reaction is monitored by thin-layer chromatography. At concluded reaction 10 ml of ethanol are added dropwise to the mixture and the ammonia is evaporated. The residue is taken up in dichloromethane, washed with water, then it is evaporated at reduced pressure. The residue is dissolved in 20 ml of ethanol and is treated in boiling solution with charcoal, then it is filtered. Subsequently a solution of 0.58 g of malonic acid, in a mixture of 10 ml of ethanol and 0.1 ml of water, is added dropwise to the filtrate. Then the solution is evaporated to half of its volume at reduced pressure. During several days of standing in the cool white crystals are formed. Yield: 0.55 g (22.5 percent).

M.p.: 160° C. (decomposition), $[\alpha]_D^{20} = +69.7°$ (c=0.2, ethanol).

EXAMPLE 3

8-beta-[Cyclopentano/3,4(4,5)/pyrazol-1-yl-methylene]-6-methyl-ergol-9-ene

Starting from 5.37 g (0.02M) of 6-methyl-8-beta-hydrazino-methyl-ergol-9-ene and 2.57 g (0.023M) of 2-formyl-cyclopentanone the procedure described in Example 1 is applied. Yield: 2.76 g (40 percent) of a crystalline product. M.p.: 235° to 237° C., $[\alpha]_D^{20} = +90.1°$ (c=0.2, ethanol).

EXAMPLE 4

8-beta-[3(5)-Methyl-cyclopentano/4,5(3,4)/pyrazol-1-yl-methylene]-6-methyl-ergoline Starting from 5.41 g (0.02M) of 8-beta-hydrazino-methyl-ergoline and 3 g (0.024M) of 2-acetyl-cyclopentanone the procedure described in Example 1 is applied. Yield: 4.9 g (68 percent) of a white, crystalline product. M.p.: 188° to 190° C., $[\alpha]_D^{20} = +101.2°$ (c=0.2, tetrahydrofuran).

EXAMPLE 5

8-beta-[3(5)-(3-Pyridyl)-cyclopentano/4,5(3,4)-/pyrazol-1-yl-methylene]-6-methyl-ergol-9-ene 5.37 g (0.02M) of 6-methyl-8-beta-hydrazino-methyl-ergol-9-ene are dissolved in 150 ml of anhydrous methanol at room temperature, then a solution of 4 g (0.021M) of 2-nicotinoyl-cyclopentanone in 20 ml of methanol is added, and subsequently at ice cooling 3.3 ml (0.024M) of boron trifluoride-acetic acid complex solution (boron trifluoride content 36 percent) are added dropwise. Cooling is discontinued and the mixture is stirred for one hour at room temperature. Then the mixture is poured over a mixture of 100 g of crushed ice and 400 ml of water, it is made alkaline with a solution of ammonium hydroxide to pH=9, and it is extracted four times with 80 ml of dichloro-methane. The combined organic layers, washed with water, are dried over sodium sulfate, and evaporated to dryness at reduced pressure. The residue obtained is purified by column chromatography according to the procedure described in Example 1. Yield: 3.5 g of a pale yellow, crystalline product. Recrystallized from methanol, m.p.: 140° to 141° C., $[\alpha]_D^{20} = +86.3°$ (c=0.2, ethanol).

Yield: 42 percent.

Preparation of the starting 2-nicotinoyl-cyclopentanone

Starting from 15.3 g (0.10M) of 1-morpholino-cyclopentene and 16.6 g (0.11M) of nicotinoyl-chloride the procedure described by Eistert is followed [Berichte 94, 2591 (1961)], yielding 9.5 g of the product (50.2 percent) as a pale yellow oil solidifying at room temperature. B.p.: 152° to 154° C./133 Pa.

EXAMPLE 6

8-beta-[3(6)-Methyl-4(5)-oxo-cyclopentano/4,5(3,4)-/pyrazol-1-yl-methylene]-6-methyl-ergol-9-ene 2.68 g (0.01M) of 6-methyl-8-beta-hydrazino-methyl-ergol-9-ene and 1.80 g (0.013M) of 2-acetyl-cyclopenta-1,3-dione are simultaneously added at vigorous stirring to 150 ml of boiling ethanol. After 4 minutes 15 ml of 2N aqueous hydrochloric acid are added in one portion to the reaction mixture which is refluxed for additional 15 minutes. Then it is poured over 200 g of crushed ice, adjusted with ammonium hydroxide to pH=9 and extracted five times with 80 ml of dichloromethane. The combined extracts are dried over sodium-sulfate, then they are evaporated to dryness at reduced pressure and the residue is purified by column chromatography, using a column prepared from 100 g of silicagel, dissolved in the eluting solvent. Elution is carried out with a 100:0.2:5 mixture of chloroform, water and methanol. Evaporating the eluates at reduced pressure yields 2.3 g of white crystals.

Yield: 62 percent.

After repeated crystallization from ethanol m.p.: 216° to 218° C., $[\alpha]_D^{20} = +100.6°$ (c=0.2, chloroform).

EXAMPLE 7

8-beta-[3(6)-Methyl-4(5)-hydroxy-cyclopentano/4,5(3,4)/pyrazol-1-yl-methylene]-6-methyl-ergol-9-ene A solution of 3.72 g (0.01M) of 8-beta-[3(6)-methyl-4(5)-oxo-cyclopentano/4,5(3,4)/pyrazol-1-yl-methylene]-6-methyl-ergol-9-ene (Example 6) in 80 ml of anhydrous tetrahydrofuran is added within 10 minutes to a vigorously stirred suspension of 0.5 g (0.013M) of lithium aluminium hydride in 200 ml of anhydrous tetrahydrofuran. The solution is refluxed at constant stirring for 20 minutes, then it is left to cool. The excess of lithium aluminium hydride is decomposed with water, 100 ml of ethanol are added, and the suspension is filtered. The filtered aluminium oxide is extracted with 100 ml of hot ethanol. The combined extracts and filtrate are evaporated to dryness at reduced pressure. 100 ml of water is added to the residue which is extracted with a mixture of chloroform-isopropanol (3:1) till the organic layer no longer gives a positive van Urk reaction. The combined organic extract is dried over sodium sulfate and evaporated to dryness at reduced pressure, yielding 3.0 g (80 percent) of white crystals. Repeated crystallization results in an m.p. of 226° to 228° C. (decomposition), $[\alpha]_D^{20} = +86.3°$ (c=0.2, ethanol).

EXAMPLE 8

8-beta-[3(6)-Methyl-4(5)-hydroxy-imino-cyclopentano/4,5(3,4)/pyrazol-1-yl-methylene]-6-methyl-ergol-9-ene 1 g (0.0027M) of 8-beta-[3(6)-methyl-4(5)-oxo-cyclopentano/4,5(3,4)/pyrazol-1-yl-methylene]-6-methyl-ergol-9-ene (Example 6) is dissolved in 100 ml of 96 percent ethanol, 1.0 g (0.014M) of hydroxylamine hydrochloride in 1 ml of water and 1.95 ml (0.014M) of triethyl amine are added and the entire mixture is refluxed for 6 hours. Then the solution is evaporated to dryness at reduced pressure. 40 ml of water are added to the residue, which is then extracted with a 3:1 mixture of chloroform and isopropanol till the organic layer no longer gives positive van Urk reaction. The combined organic layers are washed with water, dried over sodium sulfate and evaporated to dryness at reduced pressure, yielding 1 g (96 percent) of a crystalline product. Recrystallized from ethanol, the m.p. is 260° C., $[\alpha]_D^{20} = +81.3°$ (c=0.2, ethanol).

EXAMPLE 9

8-beta-[3(5)-Methyl-cyclohexano/4,5(3,4)/pyrazol-1-yl-methylene]-6-methyl-ergol-9-ene Starting from 5.37 g (0.02M) of 6-methyl-8-beta-hydrazino-methyl-ergol-9-ene and 3.0 g (0.021M) of 2-acetyl-cyclohexanone, the procedure described in Example 1 is applied, yielding 5.1 g (67 percent) of a white, crystalline product, m.p.: 173° to 175° C., $[\alpha]_D^{20} = +68.3°$ (c=0.2, ethanol).

EXAMPLE 10

8-beta-[(3(7),6(4)-Trimethyl-4(6)-oxo-cyclohexano/4,5(3,4)/pyrazol-1-yl-methylene]-6-methyl-ergol-9-ene Starting from 2.68 g (0.01M) of 6-methyl-8-beta-hydrazino-methyl-ergol-9-ene and 2.36 g (0.013M) of 2-acetyl-5,5-dimethyl-cyclohexa-1,3-dione (2-acetyl-dimedone), the procedure described in Example 6 is applied. Chromatography is carried out with an eluting solvent of 100:0.1:3 chloroform-water-methanol. Yield: 2.4 g (58 percent) of a white crystalline product. Recrystallized from ethanol m.p.: 200° C. $[\alpha]_D^{20} = +84.5°$ (c=0.2, ethanol).

EXAMPLE 11

8-beta-[3(7),6(4)-Trimethyl-4(6)-hydroxy-imino-cyclohexano/4,5(3,4)/pyrazol-1-yl-methylene]-6-methyl-ergol-9-ene 4.14 g (0.01M) of 8-beta[3(7),6(4),6(4)-trimethyl-4(6)-oxo-cyclohexano/4,5(3,4)/pyrazol-1-yl-methylene]-6-methyl-ergol-9-ene (Example 10) are dissolved in 250 ml of hot ethanol. At first 5.15 g (0.10M) of hydroxylamine hydrochloride and then 13.9 ml (0.10M) of triethylamine are added, and the entire mixture is refluxed for 30 hours. The progress of the reaction is monitored by thin-layer chromatography. The developing solvent is a 100:22:1.7 mixture of chloroform, methanol and water, while the visualizing reagent is van Urk's. When the starting material disappeares from the solution, the ethanol is evaporated at reduced pressure, 80 ml of water are added to the residue, its pH is adjusted to pH=9 with a solution of ammonium hydroxide, then the solution is extracted with a 3:1 mixture of chloroform and isopropanol till a drop of the organic phase fails to give a positive van Urk reaction. The combined organic phases are dried over sodium sulfate and subsequently evaporated to dryness at reduced pressure. The evaporation residue is dissolved in hot ethanol, decolourized with charcoal, and it is concentrated to one third of its volume. The crystals formed from the concentrated solution are filtered and dried. Yield: 3.87 g (90 percent).

M.p.: 230° C. (decomposition).

EXAMPLE 12

8-beta-[3,5-Dimethyl-pyrazol-1-yl-methylene]-6-methyl-ergol-9-ene

Starting from 5.37 g (0.02M) of 6-methyl-8-beta-hydrazino-methyl-ergol-9-ene and 2.2 g (0.022M) of pentane-2,4-dione, the procedure described in Example 1 is applied, except that insted of submitting to chromatography the evaporation residue of the dichloromethane solution, it is dissolved in 250 ml of hot ethanol and decolourized with charcoal. The crystals formed at the cooling of the solution are filtered and combined with the second crop of crystals obtained by the concentration of the mother liquor. Yield 4.64 g (70 percent) of a white, crystalline product. M.p.: 218° to 220° C., $[\alpha]_D^{20} = +72.1°$ (c=0.2, ethanol).

EXAMPLE 13

8-beta-(3,5-Dimethyl-4-ethyl-pyrazol-1-yl-methylene)-6-methyl-ergol-9-ene

Starting from 5.37 g (0.02M) of 6-methyl-8-beta-hydrazino-methyl-ergol-9-ene and 3 g (0.023M) of 3-ethyl-pentane-2,4-dione, the procedure described in Example 1 is applied. Yield: 4.5 g (62 percent) of a white, crystalline product. M.p.: 175° to 177° C., $[\alpha]_D^{20} = +61.5°$ (c=0.2, ethanol).

EXAMPLE 14

8-beta-(3,5-Dimethyl-4-allyl-pyrazol-1-yl-methylene)-6-methyl-ergol-9-ene

Starting from 5.37 g (0.02M) of 6-methyl-8-beta-hydrazino-methyl-ergol-9-ene and 3.4 g (0.024M) of 3-allyl-pentane-2,4-dione, the procedure described in Example 1 is applied. Yield: 4.5 g (60 percent) of a white, crystalline product. M.p.: 177° to 178° C., $[\alpha]_D^{20} = +63.5°$ (c=0.2, ethanol).

EXAMPLE 15

8-beta-(3-Carbethoxy-4-methyl-5-hydroxy-pyrazol-1-yl-methylene)-6-methyl-ergol-9-ene Starting from 5.37 g (0.02M) of 6-methyl-8-beta-hydrazino-methyl-ergol-9-ene and 4.85 g (0.024M) of 2-oxalyl-propionic acid diethyl ester, the procedure described in Example 1 is applied. Yield: 4.87 g of a white, crystalline product. M.p.: 150° to 151° C., $[\alpha]_D^{20} = +39.5°$ (c=0.2, ethanol).

EXAMPLE 16

8-beta-[3(5)-/2-Pyridyl/-5(3)-methyl-pyrazol-1-yl-methylene]-6-methyl-ergol-9-ene With 5.37 g (0.02M) of 6-methyl-8-beta-hydrazino-methyl-ergol-9-ene and 3.9 g (0.024M) of (2-pyridyl)-butane-1,3-dione the procedure described in Example 5 is applied. Yield: 4.0 g (50.6 percent) of a white crystalline product. M.p.: 226° to 228° C., $[\alpha]_D^{20} = = +73.8°$ (c=0.2, ethanol).

EXAMPLE 17

8-beta-[3(5)-/2-Pyridyl/-5(3)-methyl-pyrazol-1-yl-methylene]-6-methyl-ergoline

Starting from 5.41 g (0.02M) of 6-methyl-8-beta-hydrazino-methyl-ergol-9-ene and 3.9 g (0.024M) of (2-pyridyl)-butane-1,3-dione the procedure described in Example 5 is applied. Yield: 4.3 g (54 percent).

Recrystallized from a mixture of dichloroethane and chloroform m.p. 265° to 267° C.

EXAMPLE 18

8-beta-[3,5-Dimethyl-4-(1-oxo-ethyl)-pyrazol-1-yl-methylene]-6-methyl-ergol-9-ene Starting from 2.68 g (0.01M) of 6-methyl-8-beta-hydrazino-methyl-ergol-9-ene and 2.80g (0.02M) of triacetyl-methane the procedure described in Example 6 was applied. Recrystallization from ethanol yielded 1.42 g (38 percent) of the product. M.p.: 228° to 232° C., $[\alpha]_D^{20} = +78.6°$ (c=0.2, chloroform). During chromatography 0.07 g of 8-beta-(3,5-dimethyl-pyrazol-1-yl-methylene)-6-methyl-ergol-9-ene can be obtained from the last fractions as a by-product. M.p.: 218° to 220° C., $[\alpha]_D^{20} = +72.1°$ (c=0.2, ethanol). Mixed with the former product it gives significant m.p. depression.

EXAMPLE 19

8-beta-[3,5-Dimethyl-4-(1-hydroxy-ethyl)-pyrazol-1-yl-methylene]-6-methyl-ergol-9-ene Starting from 3.75 g (0.01M) of 8-beta-[3,5-dimethyl-4-(1-oxo-ethyl)-pyrazol-1-yl-methylene]-6-methyl-ergol-9-ene (Example 18) and 0.5 g (0.013M) of lithium aluminium hydride the procedure described in Example 7 is applied, yielding 2.71 g (72 percent) of the product. Recrystallized repeatedly from ethanol m.p.: 212° to 214° C., $[\alpha]_D^{20} = +40.1°$ (c=0.2, chloroform).

EXAMPLE 20

8-beta-[3,5-Dimethyl-4-(1-hydroxy-imino-ethyl)-pyrazol-1-yl-methylene]-6-methyl-ergol-9-ene Starting from 3.75 g (0.01M) of 8-beta-[3,5-dimethyl-4-(1-oxo-ethyl)-pyrazol-1-yl-methylene]-6-methyl-ergol-9-ene (Example 18), 3.48 g (0.05M) of hydroxylamine hydrochloride and 7 ml (0.05M) of triethyl amine the procedure described in Example 8 is applied, yielding 3.72 g (90 percent) of the product.

Recrystallized from 96 percent ethanol m.p. higher than 260° C. $[\alpha]_D^{20} = +37.9°$ (c=0.2, 96 percent ethanol).

EXAMPLE 21

Pharmaceutical composition

Composition of one tablet:

| | |
|---|---|
| 8-beta-[3(5)-Methyl-cyclopentano/4,5(3,4)/-pyrazol-1-yl-methylene]-6-methyl-ergol-9-ene hydrogene fumarate | 50.0 mg |
| Avicel PH 102* (microcrystalline cellulose) | 46.5 mg |
| Aerosil-200** (colloidal SiO$_2$) | 0.5 mg |
| Stearic acid (powder) | 2.5 mg |

-continued

| Magnesium stearate | 0.5 mg |
|---|---|
| | 100.0 mg |

*FMC Corporation (Pennsylvania USA)
**Begussa (FRG)

What we claim is:

1. A pyrazole with an ergoline skeleton of the formula (I)

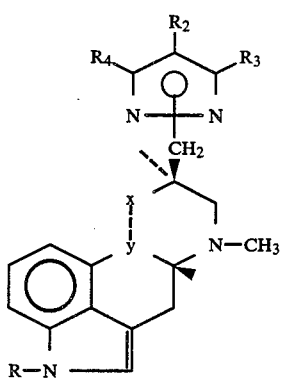

wherein x ... y stands for a

—CH=C—  or  —CH₂—CH—  group,

R is a hydrogen atom or methyl group, $R_1$ stands for a hydrogen atom, $C_{1-4}$ alkyl, carbethoxy or pyridyl-group, $R_2$ stands for a hydrogen atom, $C_{1-4}$ alkyl or, allyl, $R_3$ stands for a hydrogen atom, $C_{1-4}$ alkyl or, hydroxy group, furthermore $R_2$ and $R_3$ may stand together for a group of formula (II),

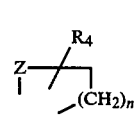

wherein

Z stands for a methylene, carbonyl, hydroxymethylene or hydroxyiminomethylene group, $R_4$ stands for a hydrogen atom or one or two $C_{1-4}$ alkyl group(s), and n is 1 or 2, and pharmaceutically acceptable salts thereof.

2. 8-beta-[3(5)-Methyl-cyclopentano/4,5(3,4)-/pyrazol-1-yl-methylene]-6-methyl-ergol-9-ene.

3. 8-beta-[3(5)-Methyl-cyclopentano/4,5(3,4)-/pyrazol-1-yl-methylene]-6-methyl-ergol-9-ene hydrogen fumarate.

4. A pharmaceutical composition for use as a $PGF_{2alpha}$ antagonist, and containing as active ingredient an effective amount of at least one compound of formula I as defined in claim 1 and a pharmaceutically acceptable solid or liquid carrier and/or additive.

5. A method of inhibiting $PGF_{2alpha}$ activity in a patient, which comprises: administering to said patient a pharmaceutical composition in a dosage form per day containing 0.5 to 3 mg/kg body weight of an active ingredient selected from the group consisting of 8-beta-[3(5)-Methyl-cyclopentano/4,5(3,4)/-pyrazol-1-yl-methylene]-6-methyl-ergol-9-ene, 8-beta[3(5)-Methyl-cyclopentano/4,5(3,4)/pyrazol-1-yl-methylene]-1,6-dimethyl-ergol-9-ene hydrogen maleinate, 8-beta-[3(5)-(3-Pyridyl)-cyclopentano/4,5(93,4)/-pyrazol-1-yl-methylene]-6-methyl-ergol-9-ene, 8-beta-[3(5)-Methyl-cyclohexano/4,5(3,4)/-pyrazol-1-yl-methylene]-6-methyl-ergol-9-ene, 8-beta-[(3(7),6(4),6(4)-Trimethyl-4(6)-oxo-cyclohexano/4,5(3,4)pyrazol-1-yl-methylene]-6-methyl-ergol-9-ene, 8-beta-[3(7),6(4),6(4)-Trimethyl-4(6)-hydroxy-imino-cyclohexano/4,5(3,4)/pyrazol-1-yl-methylene]-6-methyl-ergol-9-ene, 8-beta-(3,5-Dimethyl-4-allyl-pyrazol-1-yl-methylene)-6-methyl-ergol-9-ene, 8-beta-(3-Carbethoxy-4-methyl-5-hydroxy-pyrazol-1-yl-methylene)-6-methyl-ergol-9-ene, 8-beta-[3(5)-/2-Pyridyl/-5(3)-methyl-pyrazol-1-yl-methylene]-6-methyl-ergol-9-ene, 8-beta-[3(5)-/2-Pyridyl/-5(3)-methyl-pyrazol-1-yl-methylene]-6-methyl-ergoline, and pharmaceutically acceptable salts thereof.

* * * * *